(12) United States Patent
Wong (10) Patent No.: US 9,931,137 B2
(45) Date of Patent: Apr. 3, 2018

(54) FIXATION DEVICE

(71) Applicant: Wright Medical Technology, Inc., Memphis, TN (US)

(72) Inventor: Kian-Ming Wong, Lakeland, TN (US)

(73) Assignee: Wright Medical Technology, Inc., Memphis, TN (US)

( * ) Notice: Subject to any disclaimer, the term of this patent is extended or adjusted under 35 U.S.C. 154(b) by 499 days.

(21) Appl. No.: 14/419,819

(22) PCT Filed: Sep. 11, 2014

(86) PCT No.: PCT/US2014/055142
§ 371 (c)(1),
(2) Date: Feb. 5, 2015

(87) PCT Pub. No.: WO2016/039754
PCT Pub. Date: Mar. 17, 2016

(65) Prior Publication Data
US 2017/0224383 A1    Aug. 10, 2017

(51) Int. Cl.
*A61B 17/62* (2006.01)
*A61B 17/64* (2006.01)
*A61B 17/00* (2006.01)

(52) U.S. Cl.
CPC .......... *A61B 17/6458* (2013.01); *A61B 17/62* (2013.01); *A61B 17/645* (2013.01); *A61B 2017/00477* (2013.01)

(58) Field of Classification Search
CPC .............. A61B 17/8861; A61B 17/848; A61B 17/6458; A61B 17/62; A61B 17/645;
(Continued)

(56) References Cited

U.S. PATENT DOCUMENTS 4,923,458 A * 5/1990 Fischer ............ A61B 17/8861
606/57
4,936,843 A * 6/1990 Sohngen ............ A61B 17/6441
606/54
(Continued)

FOREIGN PATENT DOCUMENTS

GB        567715 A    2/1945
JP     S63-503119 A   11/1988
WO      87/06125 A1   10/1987

OTHER PUBLICATIONS

International Search Report and Written Opinion of the International Searching Authority issued for International patent application No. PCT/US2014/055142, dated May 22, 2015, 15 pages.
(Continued)

*Primary Examiner* — Pedro Philogene
(74) *Attorney, Agent, or Firm* — Duane Morris LLP (57) ABSTRACT

A fixation device comprises a first body having a threaded end, a longitudinal axis, and a bore perpendicular to the longitudinal axis. A second body is received in the bore. The second body has an exterior thread and an interior passage for receiving a pin or wire. The second body has a wire locking device for retaining the pin or wire. An advance nut engages the exterior thread. The advance nut abuts the first body for moving the wire locking device away from the first body when the advance nut is turned, for tensioning the pin or wire.

17 Claims, 7 Drawing Sheets

(58) Field of Classification Search
CPC ............ A61B 17/6466; A61B 17/6425; A61B 17/8869; A61B 17/60; A61B 17/6416; A61B 17/6441; A61B 17/66; A61B 17/606; A61B 2017/00477
USPC ...................................... 606/54–59; 128/898
See application file for complete search history.

(56) References Cited

U.S. PATENT DOCUMENTS

| | | | |
|---|---|---|---|
| 5,496,319 A | 3/1996 | Allard et al. | |
| 5,630,814 A * | 5/1997 | Ross, Jr. ................ | A61B 17/62 606/56 |
| 5,702,389 A | 12/1997 | Taylor et al. | |
| 5,971,984 A * | 10/1999 | Taylor .................... | A61B 17/62 128/898 |
| 6,533,785 B1 * | 3/2003 | Frigg ................. | A61B 17/6466 606/53 |
| 2007/0049930 A1 * | 3/2007 | Hearn ................... | A61B 17/66 606/56 |
| 2009/0036891 A1 * | 2/2009 | Brown ............... | A61B 17/6466 606/57 |

OTHER PUBLICATIONS

Office Action issued in connection with corresponding Canadian patent application No. 2,888,399, dated Jan. 18, 2017, 3 pages.
Office Action issued in connection with corresponding Canadian patent application No. 2,888,399, dated Mar. 22, 2016, 6 pages.
Office Action issued in connection with corresponding Australian patent application No. 2014321173, dated May 20, 2016, 5 pages.
First Office Action issued for corresponding Japanese patent application No. 2016-536226, dated Jun. 6, 2017, 4 pages.

* cited by examiner

FIXATION DEVICE

CROSS REFERENCE TO RELATED APPLICATIONS

This application is a national phase entry under 35 U.S.C. 371 of international patent application No. PCT/US14/55142, filed Sep. 11, 2014, the entirety of which is incorporated herein by reference.

FIELD

This application pertains generally to medical devices, and more particularly to a fixation device suitable for use with a circular fixator.

BACKGROUND

Most standard external fixation arthrodesis procedures use a prebuilt frame including two tibial rings and a foot plate with an extension, referred to as a circular fixator. A circular fixator system can be used for open or closed fracture fixation, pseudoarthrosis or nonunions of long bones, limb lengthening by epiphyseal or metaphyseal distraction, correction of bony or soft tissue deformities, or correction of segmental or nonsegmental bony or soft tissue defects. Circular Fixators have been used on long bones including: the tibia, fibula, femur, humerus, radius and ulna.

Prior to insertion of wires or pins, the circular fixator is positioned around the tibia and foot. The leg is eccentrically located in the frame to accommodate the posterior musculature, and the plantar aspect of the foot extends above or below the foot plate. To maintain the tibia and foot in position, folded up towels can be placed under the calf.

The surgeon inserts wires through the bones, and secures the wires to the frame using bolts that are inserted into holes in the rings and foot plate of the frame.

The surgeon then uses a wire tensioner to apply a desired tension to each individual wire.

SUMMARY

In some embodiments, a fixation device comprises: a first body having a threaded end, a longitudinal axis and a bore perpendicular to the longitudinal axis. A second body is received in the bore. The second body has an exterior thread and an interior passage for receiving a pin or wire. The second body has a wire locking device for retaining the pin or wire. An advance nut engages the exterior thread. The advance nut abuts the first body for moving the wire locking device away from the first body when the advance nut is turned, for tensioning the pin or wire.

In some embodiments, apparatus comprises: a circular fixator having at least one ring and a fixation device. The fixation device includes: a first body having a longitudinal axis, a bore perpendicular to the longitudinal axis, and a mounting device for detachably mounting the first body to the ring. A second body is received in the bore. The second body has an exterior thread and an interior passage for receiving a pin or wire. The second body has a wire locking device for retaining the pin or wire. An advance nut engages the exterior thread. The advance nut abuts the first body for moving the wire locking device away from the first body when the advance nut is turned, for tensioning the pin or wire.

In some embodiments, a method comprises: fixing a first body of a fixation device to a frame, the first body having a second body of the fixation device slidably received therein, the second body having a threaded portion; positioning a nut along the threaded portion of the second body, with the nut abutting the first body; locking the second body to a pin or wire inserted into a bone of a patient; and advancing the nut along the threaded portion of the second body, so as to tension the pin or wire.

DETAILED DESCRIPTION

This description of the exemplary embodiments is intended to be read in connection with the accompanying drawings, which are to be considered part of the entire written description. In the description, relative terms such as "lower," "upper," "horizontal," "vertical,", "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

Figure 7:
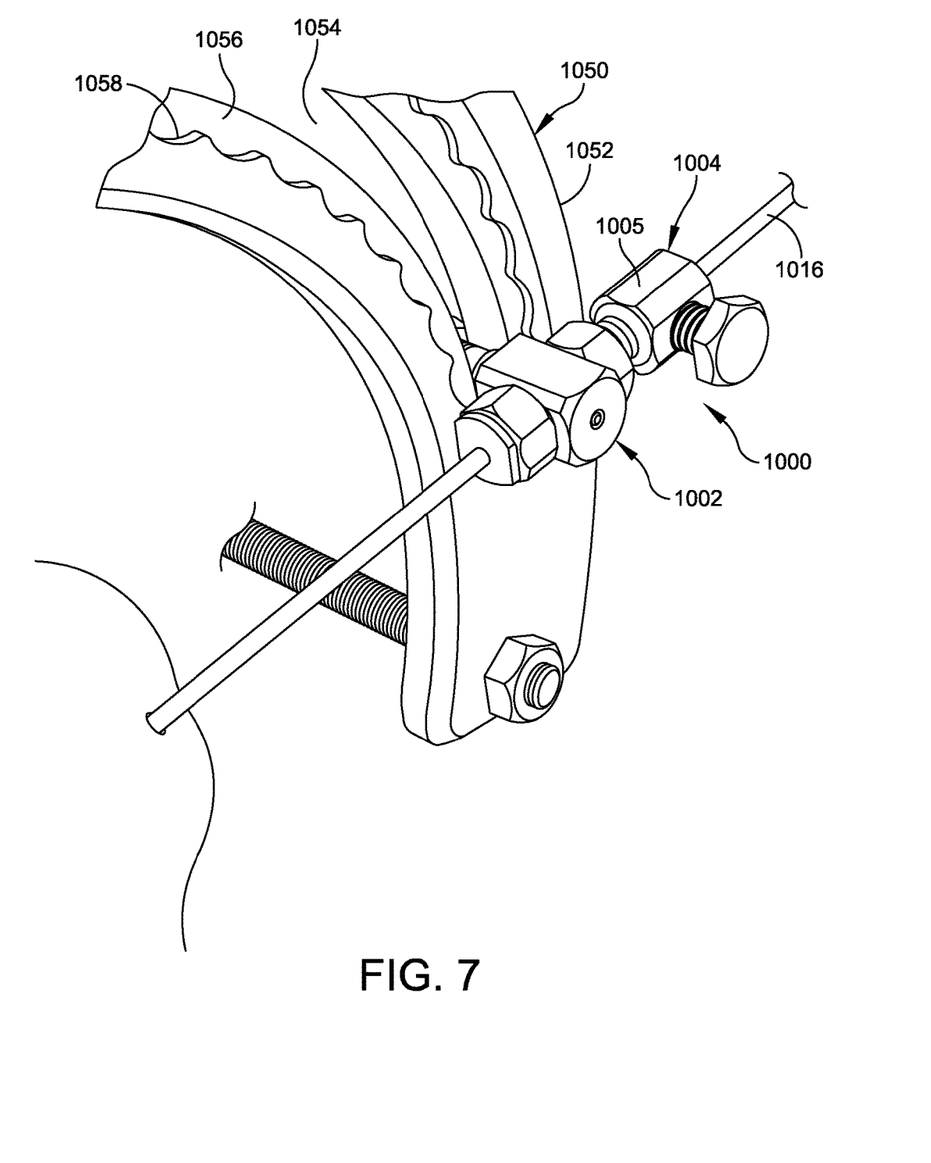
FIG. 7 is an isometric view of the wire tensioning fixation bolt of FIG. 1 attached to a circular fixator for tensioning a wire fixed to a patient's bone.

A wire tensioning fixation bolt 1000 is described herein which can be attached directly to a frame such as a circular fixator 1050 (as shown in FIG. 7), or indirectly attached to the circular fixator 1050 via an offsetting post (not shown), such that the post is attached to a ring 1052 of the circular fixator 1050, and the wire tensioning fixation bolt 1000 is attached to the post at a desired distance from the ring of the circular fixator. The wire tensioning fixation bolt 1000 has a built in tensioning mechanism. Once the wire tensioning fixation bolt 1000 is attached to the circular fixator 1050, and the wire 1016 is locked to the bolt 1000, the built-in tensioning mechanism can be activated to apply a prescribed tension to the wire, without requiring any separate wire tensioner. The wire tensioning fixation bolt 1000 can use used to fix a limb of a patient for a variety of orthopedic procedures, including Charcot, medial column fusion, fractures, and treatment of arthritis.

FIGS. 1-7 show a first embodiment of a wire tensioning fixation bolt 1000. In some embodiments, the wire tensioning fixation bolt 1000 is a fixation device comprising a first body 1002 having a threaded end 1006, a longitudinal axis 1008 and a bore 1010 perpendicular to the longitudinal axis 1008. A second body 1004 is slidably received in the bore 1010. In some embodiments, the second body 1004 includes a wire shaft body 1005 and a threaded portion 1012. The second body 1004 has an exterior threaded portion 1012 and an interior passage 1014 for receiving a pin or wire 1016. The bore 1010 of the first body is larger in diameter than the outer diameter of the threaded portion 1012 of the second body 1004, to allow the threaded portion 1012 of the second body 1004 to slide longitudinally within the bore 1010, without engaging the threads of the threaded portion 1012. The second body 1004 has a wire shaft body 1005 with a wire locking device 1018 for retaining the pin or wire 1016 in fixed relationship to the second body 1004. An advance nut 1020 engages the exterior thread 1012 of the second body 1004. The advance nut 1020 abuts the first body 1002. Rotation of the advance nut moves the threaded portion of the second body 1002, for moving the wire locking device 1018 away from the first body 1002, for tensioning the pin or wire 1016.

Figure 5:
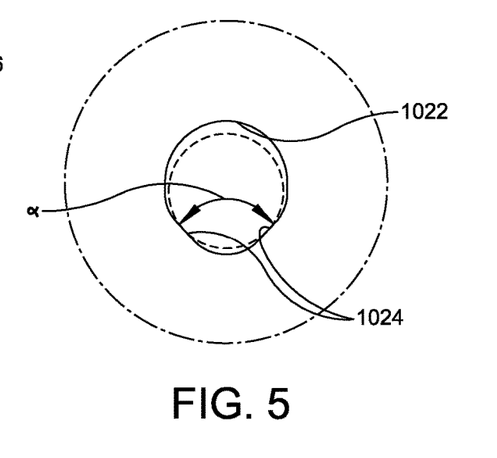
FIG. 5 is an enlarged detail of FIG. 4.

In some embodiments, the interior passage 1014 of the second body 1004 has at least one curved surface 1022 and at least one flat surface 1024. In some embodiments, as best seen in FIG. 5, the interior passage 1022 is approximately tear-drop shaped. In some embodiments, the interior passage 1014 has two flat surfaces 1024 with an angle α therebetween. In some embodiments, the angle α is in a range from about 30 degrees to about 170 degrees between the two flat surfaces. In some embodiments, the range is from about 30 degrees to about 135 degrees. For example, angle α could be 27, 33, 45, 47, 132, or 167. The two flat surfaces 1024 provide for three points of contact between the pin or wire 1016, the interior passage 1022, and the locking bolt 1026 of wire locking device 1018. The locking bolt 1026 can have a flat end surface for engaging the pin or wire 1016.

In some embodiments, the wire locking device 1018 comprises a locking bolt 1026 threadably received by the second body 1004, and positioned for forcing the pin or wire 1016 against the at least one flat surface 1024 when the locking bolt 1026 is advanced.

Figure 3:
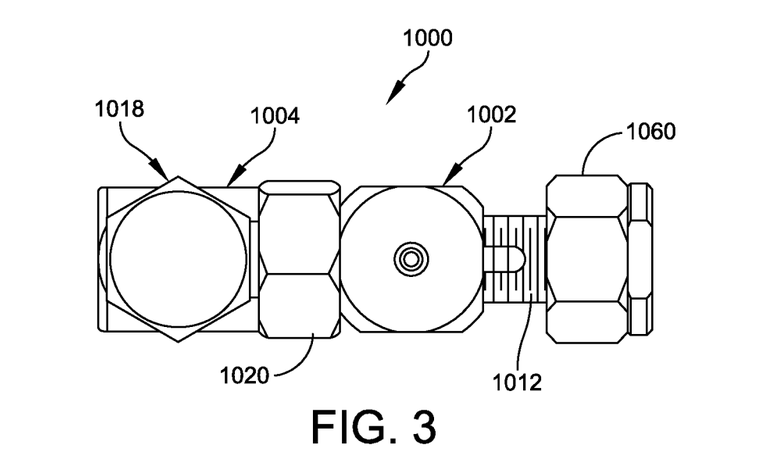
FIG. 3 is a top plan view of the wire tensioning fixation bolt of FIG. 1.
Figure 4:
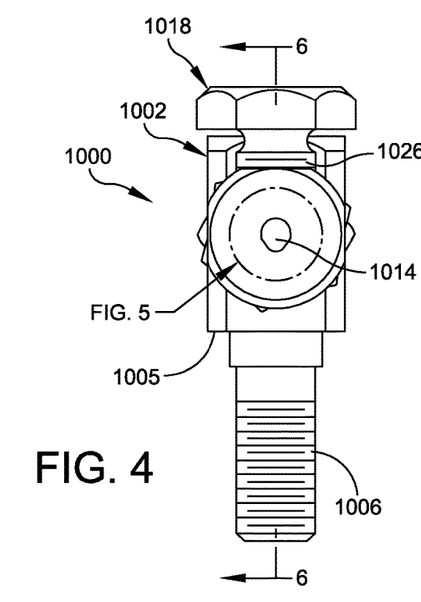
FIG. 4 is a front elevation view of the wire tensioning fixation bolt of FIG. 1.
Figure 6:
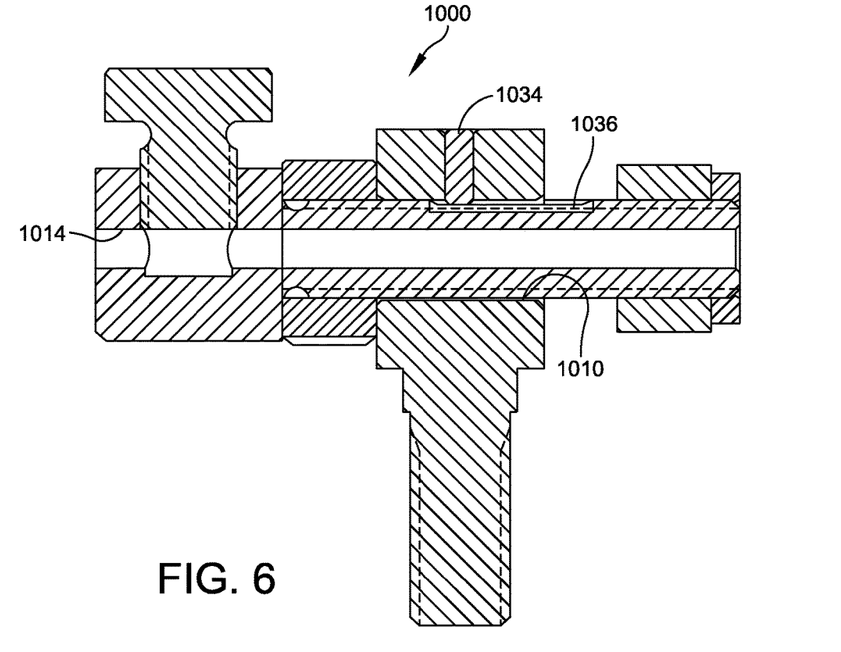
FIG. 6 is a cross sectional view taken along section line 6-6 of FIG. 4.

In some embodiments, as best seen in FIGS. 3 and 6, the second body 1004 has a groove or flat surface 1036 on the threaded portion 1012 of the second body 1004. The first body 1002 has a pin 1034 for engaging the groove or flat surface 1036. The pin 1034 limits rotation of the second body 1004 (about the longitudinal axis of the threaded portion 1012) relative to the first body 1002 to a predetermined angle (e.g., an angle from 10 degrees to 20 degrees), while permitting the second body 1004 to translate relative to the first body 1002.

FIG. 7 is an isometric view showing the wire tensioning fixation bolt 1000 attached directly to a circular fixator 1052. In some embodiments, the apparatus comprises: a circular fixator 1050 having at least one ring 1052 and a wire tensioning fixation bolt 1000. The wire tensioning fixation bolt 1000 includes: a first body 1002 having a longitudinal axis 1008, a bore 1010 perpendicular to the longitudinal axis 1008, and a mounting device 1006 for detachably mounting the first body 1002 to the ring 1052. In the example of FIG. 7, the circular fixator 1050 has a ring 1050 with an elongated slot 1054. The ring 1050 has a recessed surface 1056 on a top surface of the ring 1050, adjacent to each side of the slot 1054. In some embodiments, the ring 1050 has a plurality of scallops or pockets 1058 for receiving one or more fixation devices, such as the wire tensioning fixation bolt 1000 and/or other wire fixation devices. The wire tensioning fixation bolt 1000 can be used with other types of circular fixator, such as a frame having rings with fixed mounting holes (e.g., "SIDEKICK®" circular fixator, sold by Wright Medical Technologies of Memphis, Tenn.).

A second body 1004 is slidably received in the bore 1010 of the first body. The second body 1004 has an exterior thread 1012 and an interior passage 1014 for receiving a pin or wire 1016. The exterior thread 1012 is engaged by the nut 1020, but is not engaged by the smooth surface of bore 1010. Thus, the second body 1004 can slide freely within the bore 1010. The advance nut 1020 engages the exterior thread 1012 and abuts the first body 1002. When the nut 1020 is advanced along the thread 1012 toward the jam nut 1060 (and away from the wire shaft body 1005), the second body 1004 moves in the opposite direction, so that the wire shaft body 1005 moves away from the first body 1002. When the advance nut 1020 is rotated, it moves the wire locking device 1018 away from the first body 1002, for tensioning the pin or wire 1016. The jam nut 1060 limits travel of the advance nut 1020, and thus limits the elongation of the pin or wire 1016. Thus, the jam nut 1060 limits the amount of tension that can be applied to the pin or wire 1016 by advancing the advance nut 1020. The second body 1004 has a wire locking device 1018 for retaining the pin or wire 1016.

In the example shown in FIG. 7, the interior passage 1014 has two flat surfaces 1024 with an angle α therebetween. The angle α is in a range from about 45 degrees to about 135 degrees between the two flat surfaces 1024. The wire locking device 1018 comprises a locking bolt 1026 threadably received by the second body 1004, and positioned for forcing the pin or wire 1016 against the at least one flat surface 1024 when the locking bolt 1026 is advanced.

Figure 8:
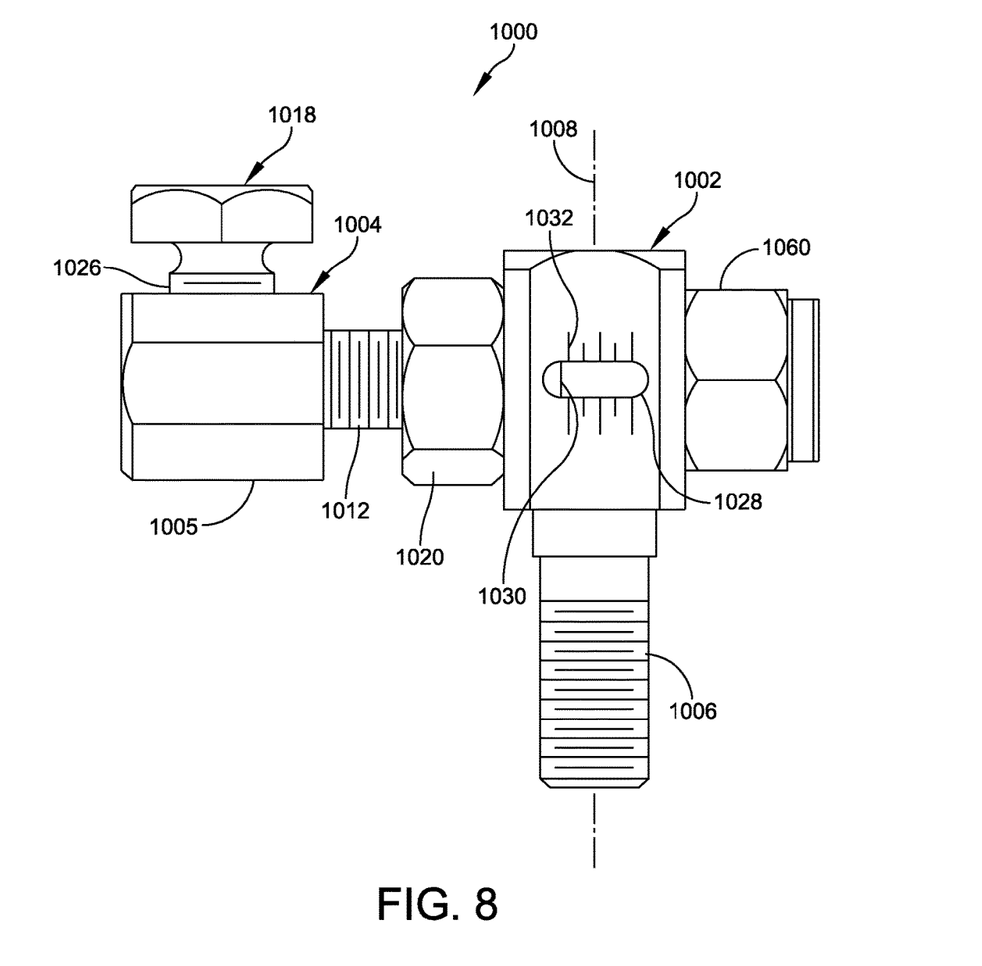
FIG. 8 is a side elevation view of a variation of the wire tensioning fixation bolt of FIG. 1, having calibration markings.

In some embodiments, as shown in FIG. 8, the first body 1002 has an opening 1028 in a side or top surface thereof, and the second body 1004 has a feature 1030 exposed within the opening 1028. The feature includes a pin or mark 1030 affixed to a side of the second body 1004, and the first body 1002 has a plurality of calibration markings 1032 adjacent the opening 1028. If a pin is used, the pin can be flush with the surface of the first body 1002 or recessed. Alternatively, feature 1030 can be a laser mark similar to laser marks 1032. A change in position of the feature 1030 relative to the opening 1028 is indicative of an elongation of the pin or wire 1016 due to the tensioning. For example, the difference in position of the feature 1030 relative to the calibration markings 1032 before and after advancing the nut 1020 away from the wire shaft body 1005 corresponds to elongation due to tension. Given the original length of the pin or wire 1016 the tension can be calculated by the following equation:

$$T = E \epsilon A \qquad (1)$$

where T is the tension force, E is the (Young's) elastic modulus of the material of the pin or wire, $\epsilon$ is the strain, i.e., the ratio of the elongation to the original length of the pin or wire ($\Delta L/L$), L is the original length, $\Delta L$ is the elongation, and A is the cross-sectional area of the pin or wire. The elongation can be measured by counting the number of markings 1032 passed by the features 1030 during tensioning.

In some embodiments, the device is calibrated by taking at least one elongation measurement for a given pin or wire 1016 of a given material. Since all of the terms in the right hand side of equation (1) are constants, except for ϵ, equation (1) can be rewritten as:

$$T=K\Delta L/L$$

where K is a constant, given by K=EA. Given a calibration measurement of the tension force T and corresponding strain (ΔL/L), K can be calculated by K=T/(ΔL/L). Subsequently, for any pin or wire 1016 of the same material and length, the distance by which the nut 1020 and wire shaft body 1005 are advanced to achieve a desired tension $T_d$ is given by $\Delta L = T_d L/K$.

The second body 1004 has a groove or flat surface 1036, and the first body 1002 has a pin 1034 for engaging the groove or flat surface 1036, so as to permit the second body 1004 to translate relative to the first body 1002. The pin 1034 is positioned to limit rotation of the second body 1004 relative to the first body 1002 to a predetermined angle, such as 10 to 20 degrees.

The wire tensioning fixation bolt 1000 can be made of a variety of materials, such as, but not limited to, stainless steel, aluminum, or titanium.

In some embodiments, a fixation method comprises positioning a first body 1002 of a wire tensioning fixation bolt 1000 on a frame, such as a circular fixator 1050. The wire tensioning fixation bolt 1000 has a first body 1002 and a second body 1004 slidably received in the first body.

The first body 1002 of the wire tensioning fixation bolt 1000 is fixed to a ring 1052 of the frame 1050 (e.g., circular fixator 1050). In some embodiments, the first body 1002 has a bolt 1006 and is fixed to the frame 1050 with a nut.

The wire tensioning fixation bolt 1000 is positioned on the frame, so that a wire locking device 1018 of a wire shaft body 1005 of the second body 1004 is positioned radially outward, away from the center of the ring 1052, and thus away from the patient's limb. The arrangement of the wire tensioning fixation bolt 1000 on the frame 1050 is shown in FIG. 7.

The first body 1002 has a second body 1004 of the wire tensioning fixation bolt 1000 slidably received therein. The second body 1004 has a threaded portion 1012. The second body 1004 can slide longitudinally within the bore 1010 of the first body 1002. The threaded portion 1012 has a flat portion or groove 1036. The alignment member or pin 1036 permits longitudinal motion of the second body 1004, while preventing rotation beyond a small predetermined value (e.g., 10 to 20 degrees).

Figure 2:
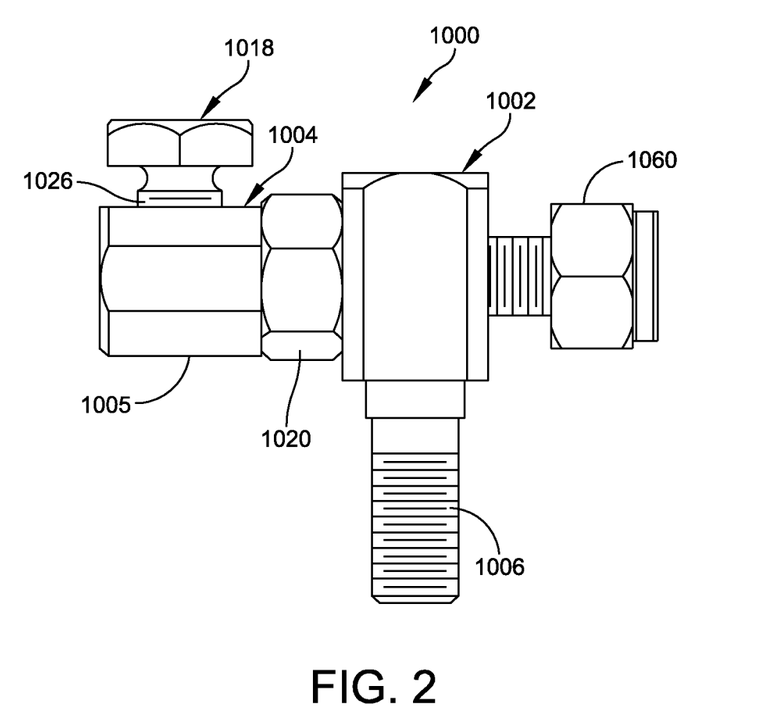
FIG. 2 is a side elevation view of the wire tensioning fixation bolt of FIG. 1.

The nut is retracted towards the wire shaft body 1005 of the second body 1004. The nut 1020 and wire shaft body 1005 are moved along the threaded portion 1012 of the second body 1004, all the way (radially inward) towards the first body 1002, until the nut 1020 abuts the first body 1002, and the wire shaft body 1005 abuts the nut 1020. This position is shown in FIGS. 2, 3 and 6. This is a fully retracted position, which allows the surgeon the greatest range of tension.

The second body 1004 is locked to a pin or wire 1016 inserted into a bone of a patient. In some embodiments, the locking step includes inserting the pin or wire 1016 through a passage 1014 in the second body 1004, and driving a locking member 1026 against a side surface of the pin or wire 1016. In some embodiments, the driving step includes driving a wire locking bolt 1026 through a threaded passage or opening 1062 in the second body 1004. In some embodiments, the passage 1010 has two flat surfaces 1024 oriented at oblique angles with respect to an axis 1064 of the locking member, and the driving step includes gripping the pin or wire 1016 between the locking member (bolt) 1026 and the two flat surfaces 1024.

With the first body 1002 secured to the frame 1050, and the second body 1004 in its fully retracted position (FIGS. 2, 3 and 6), locked to the pin or wire 1016, the wire tensioning fixation bolt 1000 is ready to tension the pin or wire 1016. The nut 1020 is advanced along the threaded portion 1012 of the second body 1004, towards the first body 1002, and away from the wire shaft body 1005. The step of advancing the nut increases a distance between the first body 1002 and the locking member 1018 of the second body 1004. This causes the wire shaft body 1005 to move radially outward from the patient's limb (e.g., foot), so as to tension the pin or wire 1016. In some embodiments, the second body 1004 has a groove or flat surface 1036, and the first body 1002 has a pin or alignment member 1034 for engaging the groove or flat surface 1036, and the step of advancing the nut 1020 includes translating the second body 1004 relative to the first body 1002 to increase a distance between the first body and the locking member, while the pin 1034 limits rotation of the second body 1004 relative to the first body 1002 to a predetermined angle α.

In some embodiments, the first body 1002 has an opening 1028 in a side or top surface thereof, and the second body 1004 has a feature 1030 exposed within the opening 1028. The position of the feature 1030 relative to the opening 1028 is indicative of an elongation of the pin or wire 1016 due to the tensioning. In some embodiments, the feature includes a pin affixed to a side of the second body. In some embodiments, the first body has a plurality of calibration markings adjacent the opening.

Figure 1:
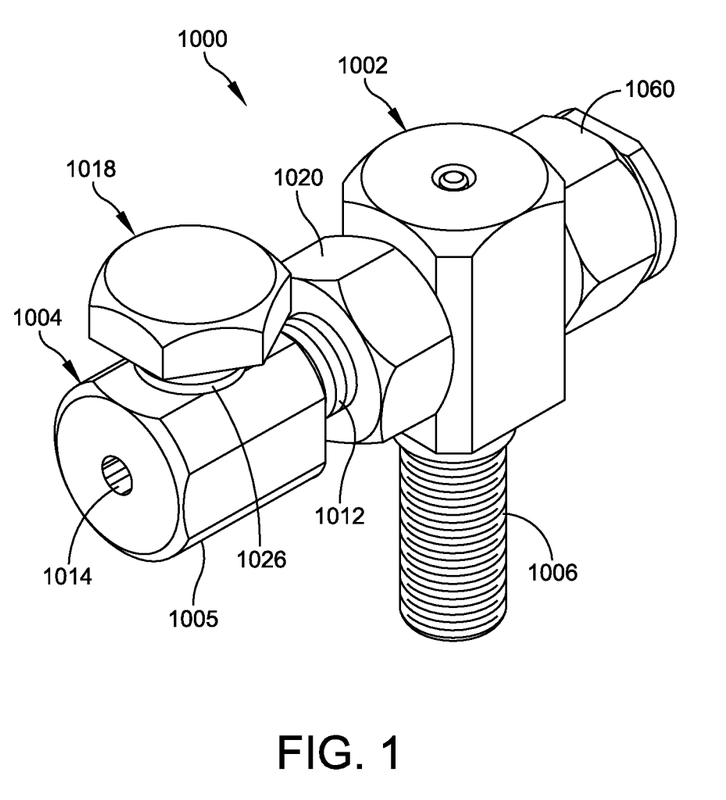
FIG. 1 is an isometric view of an embodiment of a wire tensioning fixation bolt.
Figure 9:
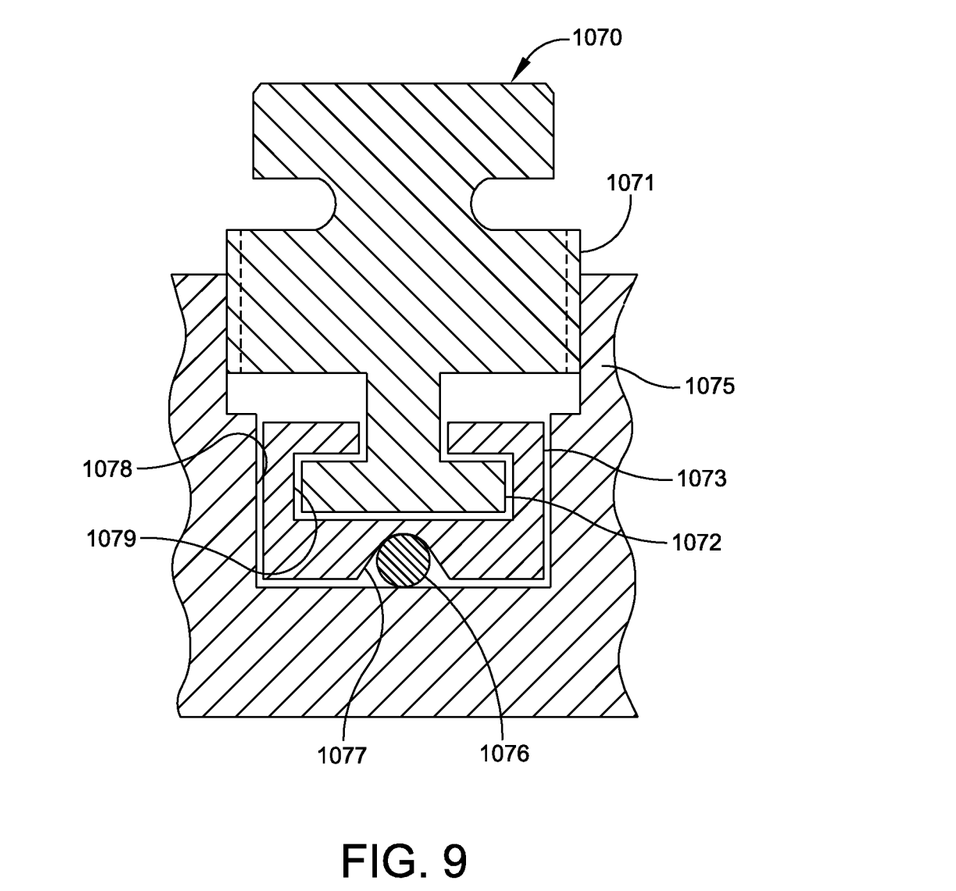
FIG. 9 is a cross section of a second embodiment of a wire locking device for the fixation bolt.
Figure 10:
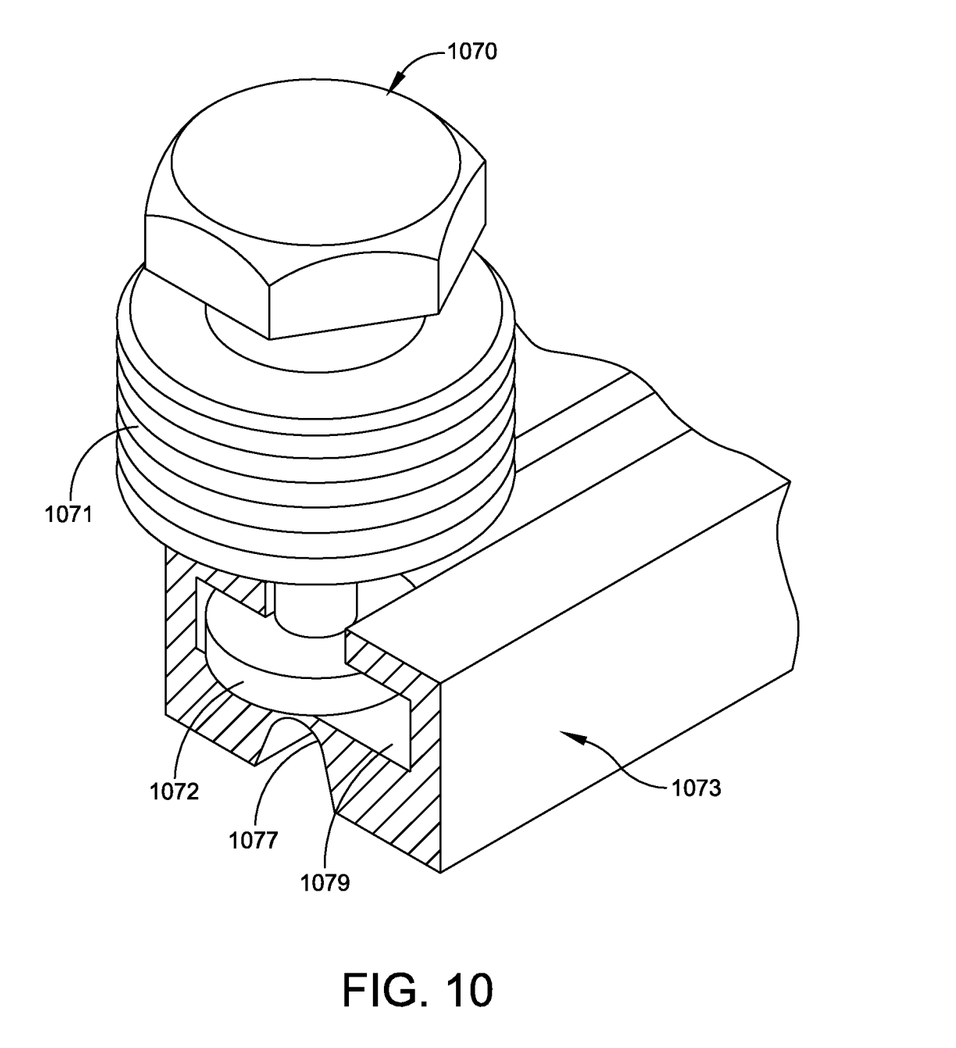
FIG. 10 is an isometric view of the locking device of FIG. 9.

FIGS. 9 and 10 show a second embodiment of a locking device 1070, which can be included in place of the locking device 1018. In the embodiment of FIGS. 9 and 10, the wire shaft body 1005 of FIG. 1 is replaced by a wire shaft body 1075 having a rectangular channel 1078. The locking device 1070 has two components: a rotating inner portion having a threaded member 1071 attached to a T-member 1072 having a T-shaped cross section. The T-member 1072 can have a disk shaped bottom portion forming the T-shaped cross-section. A rectangular outer portion 1073 has a T-shaped channel 1079 adapted to receive the T-member 1072. The rectangular outer portion 1073 is adapted to translate up and down within the rectangular channel 1078 without rotating. When the user rotates the threaded member 1071, the threaded member 1071 and T-member 1072 advance or retract in the vertical direction, causing the rectangular outer portion 1073 to rise or descend. The rectangular outer portion 1073 has a V-shaped or curved groove 1077 on its bottom surface to engage and apply a locking force against the pin or wire 1016. This method helps to prevent damage to the pin or wire 1016 while tightening the threaded member 1071, because the groove 1077 of the rectangular outer portion 1073 (which contacts the pin or wire 1016) only translates up and down while loosening or tightening of the threaded member 1071.

Although the subject matter has been described in terms of exemplary embodiments, it is not limited thereto. Rather, the appended claims should be construed broadly, to include other variants and embodiments, which may be made by those skilled in the art.

What is claimed is:

1. A fixation device, comprising:
    a first body having a threaded end, a longitudinal axis and a bore perpendicular to the longitudinal axis;

a second body received in the bore, the second body having an exterior thread and an interior passage for receiving a pin or wire, the interior passage having at least one curved surface and at least one flat surface;

a wire locking device for retaining the pin or wire, wherein the wire locking device comprises a locking bolt threadably received by the second body, the locking bolt configured for translation relative to the interior passage for forcing the pin or wire against the at least one flat surface when the locking bolt is advanced; and an advance nut engaging the exterior thread, the advance nut abutting the first body for moving the wire locking device away from the first body when the advance nut is turned, for tensioning the pin or wire.

2. The fixation device of claim 1, wherein the interior passage has two flat surfaces with an angle therebetween from about 45 degrees to about 135 degrees between the two flat surfaces.

3. The fixation device of claim 1, wherein the first body has an opening in a side or top surface thereof, and the second body has a feature exposed within the opening, the position of the feature relative to the opening being indicative of an elongation of the pin or wire due to the tensioning.

4. The fixation device of claim 3, wherein the first body has a plurality of calibration markings adjacent the opening.

5. The fixation device of claim 1, wherein:

the second body has a groove or flat surface, and the first body has a pin for engaging the groove or flat surface, so as to permit the second body to translate relative to the first body.

6. The fixation device of claim 5, wherein the pin limits rotation of the second body relative to the first body to a predetermined angle.

7. The fixation device of claim 1, wherein:

the interior passage has two flat surfaces with an angle therebetween from about 45 degrees to about 135 degrees between the two flat surfaces, the first body has an opening in a side or top surface thereof, and the second body has a feature exposed within the opening, and the first body has a plurality of calibration markings adjacent the opening, the position of the feature relative to the opening being indicative of an elongation of the pin or wire due to the tensioning, and the second body has a groove or flat surface, and the first body has a pin for engaging the groove or flat surface, so as to permit the second body to translate relative to the first body, the pin positioned to limit rotation of the second body relative to the first body to a predetermined angle.

8. The fixation device of claim 1, further comprising a jam nut threadably engaged with the exterior thread of the second body, wherein the jam nut limits translation of the second body with respect to the first body.

9. Apparatus, comprising:

a circular fixator having at least one ring; and a fixation device, including:

a first body having a longitudinal axis, a bore perpendicular to the longitudinal axis, and a mounting device for detachably mounting the first body to the ring;

a second body received in the bore, the second body having an exterior thread and an interior passage for receiving a pin or wire, the interior passage having at least one curved surface and at least one flat surface;

a wire locking device for retaining the pin or wire, wherein the wire locking device comprises a locking bolt threadably received by the second body, the locking bolt configured for translation relative to the interior passage for forcing the pin or wire against the at least one flat surface when the locking bolt is advanced; and an advance nut engaging the exterior thread, the advance nut abutting the first body for moving the wire locking device away from the first body when the advance nut is turned, for tensioning the pin or wire.

10. The apparatus of claim 9, wherein:

the interior passage has two flat surfaces with an angle therebetween from about 45 degrees to about 135 degrees between the two flat surfaces, the first body has an opening in a side or top surface thereof, and the second body has a feature exposed within the opening, the feature including a pin affixed to a side of the second body, and the first body has a plurality of calibration markings adjacent the opening, the position of the feature relative to the opening being indicative of an elongation of the pin or wire due to the tensioning, and the second body has a groove or flat surface, and the first body has a pin for engaging the groove or flat surface, so as to permit the second body to translate relative to the first body, the pin positioned to limit rotation of the second body relative to the first body to a predetermined angle.

11. A method comprising:

fixing a first body of a fixation device to a frame, the first body having a second body of the fixation device slidably received therein, the second body having a threaded portion;

positioning a nut along the threaded portion of the second body, with the nut abutting the first body;

inserting a pin or wire that is inserted in a bone of a patient through an interior passage in the second body, wherein the interior passage has at least one curved surface and at least one flat surface;

locking the second body to the pin or wire with a wire locking device, wherein the wire locking device comprises a locking bolt threadably received by the second body, the locking bolt configured for translation relative to the interior passage for forcing the pin or wire against the at least one flat surface when the locking bolt is advanced; and advancing the nut along the threaded portion of the second body, so as to tension the pin or wire.

12. The method of claim 11, wherein:

the interior passage has two flat surfaces oriented at oblique angles with respect to an axis of the locking bolt, and the locking step includes gripping the pin or wire between the locking bolt and the two flat surfaces.

13. The method of claim 11, wherein the driving step includes driving the locking bolt through a threaded opening in the second body.

14. The method of claim 11, wherein the step of advancing the nut increases a distance between the first body and the locking bolt.

15. The method of claim 11, wherein the second body has a groove or flat surface, and the first body has a pin for engaging the groove or flat surface, and the step of advancing the nut includes translating the second body relative to the first body while the pin limits rotation of the second body relative to the first body to a predetermined angle.

16. The method of claim 11, wherein the frame is a circular fixator.

17. The method of claim 11, wherein:
the passage has two flat surfaces oriented at oblique angles with respect to an axis of the locking bolt, and the locking step includes:
driving the locking bolt through a threaded opening in the second body so as to grip the pin or wire between the locking bolt and the two flat surfaces,
wherein the second body has a groove or flat surface, and the first body has an alignment member for engaging the groove or flat surface, and the step of advancing the nut includes translating the second body relative to the first body to increase a distance between the first body and the locking bolt, while the alignment member limits rotation of the second body relative to the first body to a predetermined angle.

* * * * *